United States Patent
Werner et al.

(10) Patent No.: US 7,675,045 B1
(45) Date of Patent: Mar. 9, 2010

(54) 3-DIMENSIONAL IMAGING AT NANOMETER RESOLUTIONS

(75) Inventors: James H. Werner, Los Alamos, NM (US); Peter M. Goodwin, Los Alamos, NM (US); Andrew P. Shreve, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 12/248,834

(22) Filed: Oct. 9, 2008

(51) Int. Cl.
   *G01N 21/64* (2006.01)
(52) U.S. Cl. .............................. 250/458.1; 250/459.1
(58) Field of Classification Search .............. 250/458.1, 250/459.1
   See application file for complete search history.

(56) References Cited

U.S. PATENT DOCUMENTS

| | | | | |
|---|---|---|---|---|
| 5,418,371 A | * | 5/1995 | Aslund et al. | 250/458.1 |
| 5,485,530 A | * | 1/1996 | Lakowicz et al. | 382/191 |
| 6,344,653 B1 | * | 2/2002 | Webb et al. | 250/458.1 |
| 6,710,901 B2 | * | 3/2004 | Pastor | 359/4 |
| 2008/0290263 A1 | * | 11/2008 | Feng et al. | 250/234 |

OTHER PUBLICATIONS

Eric Betzig et al., "Imaging Intracellular Fluorescent Proteins at Nanometer Resolution," Science 313 (Sep. 15, 2006), pp. 1641-1645.

Marc Schneider et al., "Two-Photon Activation and Excitation Properties of PA-GFP in the 720-920-nm Region," Biophysical J. 89 (Aug. 2005), pp. 1346-1352.

Winfried Denk et al., "Two-Photon Laser Scanning Fluorescence Microscopy," Science 248 (Apr. 6, 1990), pp. 73-76.

T.J. Mitchison, " Polewards Microtubule Flux in the Mitotic Spindle Evidence from Photoactivation of Fluorescence," J. Cell Biology 109 (1989), pp. 637-652.

M. Dahan et al, "Time-Gated Biological Imaging by use of Colloidal Quantum Dots," Optics Letters 26 (Jun. 1, 2001), pp. 825-827.

Kao et al., "Tracking of Single Fluorescent Particles in Three Dimensions: Use of Cylindrical Optics to Encode Particle Position," Biophysical J. 67 (Sep. 1994), pp. 1291-1300.

Huang et al., "Three-Dimensional Super-Resolution Imaging by Stochastic Optical Reconstruction Microscopy," 319 Science (Feb. 8, 2008), pp. 810-813.

G. Lessard et al., "Three Dimensional Tracking of Individual Quantum Dots," Appl. Phys. Letts., 91 (2007), pp. 224106-224108.

* cited by examiner

*Primary Examiner*—David P Porta
*Assistant Examiner*—Mark R Gaworecki
(74) *Attorney, Agent, or Firm*—Samuel M. Freund; Cochran Freund & Young LLC

(57) ABSTRACT

An apparatus and method for enabling precise, 3-dimensional, photoactivation localization microscopy (PALM) using selective, two-photon activation of fluorophores in a single z-slice of a sample in cooperation with time-gated imaging for reducing the background radiation from other image planes to levels suitable for single-molecule detection and spatial location, are described.

10 Claims, 1 Drawing Sheet

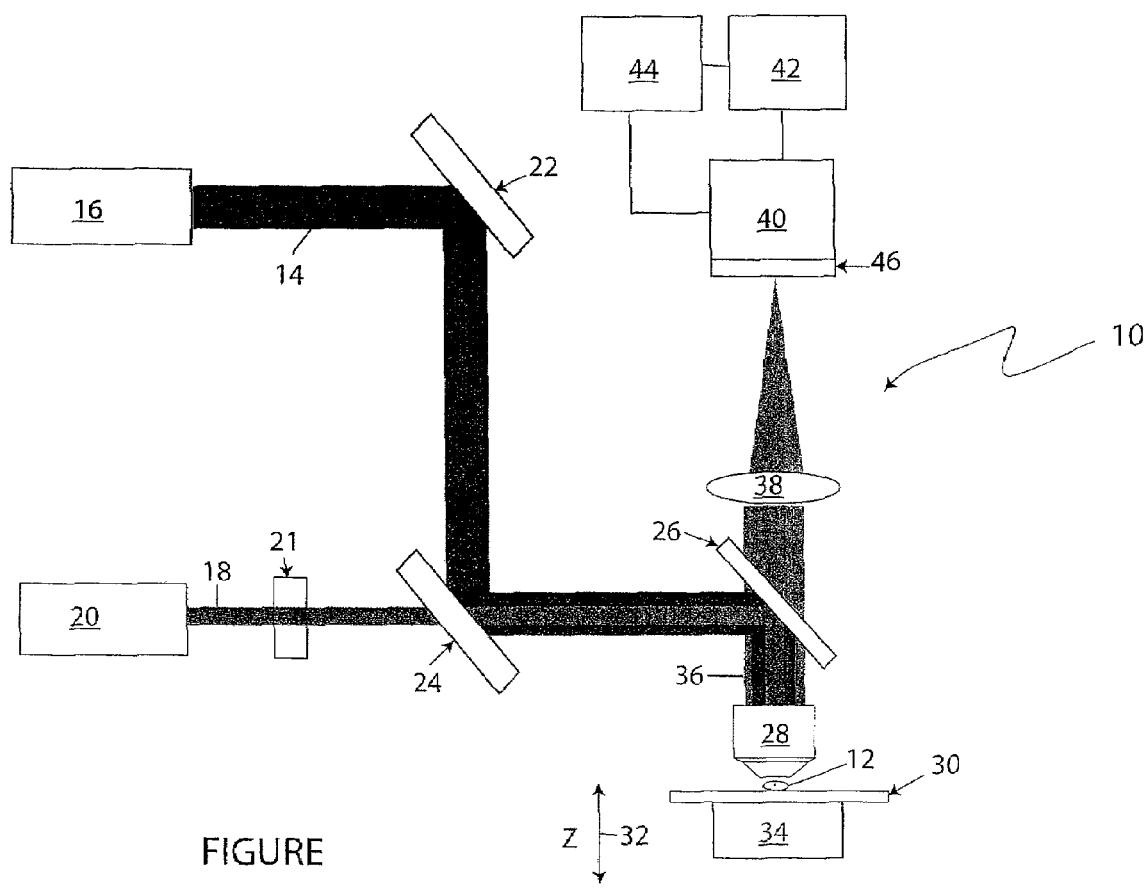
FIGURE

3-DIMENSIONAL IMAGING AT NANOMETER RESOLUTIONS

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to imaging heterogeneous materials and, more particularly, to 3-dimensional imaging having nanometer resolutions.

BACKGROUND OF THE INVENTION

X-ray diffraction and other scattering techniques (e.g. neutron diffraction) are powerful characterization tools for providing 3-dimensional structural information on the scale of atoms for crystalline materials. Such coherent scattering methods fail for many soft, disordered materials, and optical methods for structural determination, such as laser scanning confocal fluorescence microscopy, are used to determine 3-dimensional structure at length scales >1 μm. However, at smaller length scales, optical methods are limited in resolution by the wavelength of light used for observation (approximately 500 nm for visible light).

Optical microscopy methods exceeding the diffraction limit of light by relying on the fact the central position of a single fluorescent molecule (fluorophore) can be determined to a much higher accuracy (presently, having precision ~2 nm) than the width of its diffraction-limited image have been investigated, and will likely attain wide-spread use in the exploration of the finer details of cellular structure. In addition to biological structures, these single-molecule localization microscopy techniques hold promise for nano-scale imaging of many materials. In contrast to electron microscopy, single molecule localization microscopy is applicable to materials that have little or no contrast in electron density and for materials immersed in a wet or aqueous environment. Moreover, in contrast to surface-specific scanning probe techniques, such as near-field scanning optical microscopy, single-molecule localization microscopy has the potential for enabling full 3-D imaging of materials at near nanometer resolution.

As an example, while quantum dots have a diameter of 10 nm, diffraction blurs the image of a single quantum dot into a circular "blob" a few hundred nanometers across. However, one can determine the central position of the blob to a much greater accuracy than the width of the blob, with 2 nm resolution obtainable under certain favorable circumstances. Using the fact that a single fluorophore can be located in 2 dimensions with this high accuracy, one can generate a pseudo image using known calculation techniques, such that each point in this new image has a width given by the uncertainty in the determining the central position of the original diffraction limited spot. When these localization methods are combined with a method for selectively activating a small number of fluorophores for imaging, high resolution images (in two spatial dimensions) that reflect the underlying molecular density can be obtained.

Photo-activated or photo-switchable fluorophores and single-molecule detection are utilized for such high-resolution imaging methods, as molecules must be individually imaged such that their diffraction limited spots do not overlap in the image plane. For structures densely labeled with a fluorescent species, imaging individual molecules is accomplished by using a photo-activatible or photo-switchable fluorescent reporter, such as photo-activatible green fluorescent protein, PA-GFP. PA-GFP is normally in a dark (non-fluorescent) state, but can be activated into a fluorescent state upon excitation with ultra-violet radiation. In photoactivation localization microscopy, (PALM), these photoswitchable proteins are fused to a structural protein of interest. A weak UV light pulse is then applied to activate only a few molecules. These molecules are imaged, their central locations calculated, and the activated molecules are subsequently photo-bleached. Another UV light pulse is then applied to activate a few more molecules, beginning another imaging cycle. This activation, imaging, and bleaching process is repeated many times. The results from each imaging cycle are combined to form a composite pseudo-image from the entire data set. A review of the PALM procedure may be found in "Imaging Intracellular Fluorescent Proteins At Nanometer Resolution" by Eric Betzig et al. in Science 313 (15 Sep. 2006), 1642-1645, wherein photoactivatable green fluorescent protein (PA-GFP) was employed. The single-molecule localization microcopy method of Betzig et al. was limited to 2D slices.

In addition to activation of PA-GFP with ultraviolet radiation, one can also activate this molecule via two-photon excitation methods. In this activation method, two photons of near-infrared wavelengths (~800 nm) are used to convert the chromophore from a non-fluorescent to a fluorescent state. The two-photon activation of PA-GFP was recently demonstrated in "Two-Photon Activation And Excitation Properties Of PA-GFP In The 720-920-nm Region" by Marc Schneider et al. in Biophysical J. 89 (August 2005) 1346-1352. Further, in "Two-Photon Laser Scanning Fluorescence Microscopy" by Winfried Denk et al. in Science 248 (6 Apr. 1990) 73-76, molecular excitation by the simultaneous absorption of two photons in laser scanning fluorescence microscopy is described.

Another useful photoactivatable molecule is caged fluorescein which has large nitrophenyl rings that cleave off the molecule upon excitation with UV light, increasing the fluorescence quantum yield of the fluorophore ~500 fold. See, e.g., T. J. Mitchison in "Polewards Microtubule Flux In The Mitotic Spindle Evidence From Photoactivation Of Fluorescence," J. Cell Biology 109 (1989) 637-652. Caged fluorescein has a bright/dark ratio of 500:1, whereas PA-GFP has a ratio closer to 100:1. This superior bright/dark ratio for caged fluorescein is one reason this molecule is a promising contrast reagent for high resolution localization microscopy. Other reasons include the fact that caged fluorescein is commercially available (with or without an amine-reactive linker), and there is a large difference in fluorescence lifetimes between the caged (dark) and uncaged (bright) forms of this molecule. The fluorescence lifetime of the caged/quenched dye is ~210 ps, whereas the activated fluorophore has a fluorescence lifetime of 3.4 ns. This difference in fluorescence lifetime means time-gating can dramatically reduce the contribution of un-activated molecules to the background; for example, if one applies a >2-ns time-gate to the data, the fraction of photons that pass through the time-gate for the activated molecule is ~0.55 ($e^{-2/3.4}$), whereas the fraction of the photons that pass through the time-gate for the un-activated (quenched) fluorophores also present in the field of view is almost four orders of magnitude less, ~0.00007 ($e^{-2/0.21}$). This reduction in background is essential for high-resolution imaging of samples densely labeled with fluorescent reporters, as will be encountered in any sample labeled with the appropriate contrast agent throughout a volume of hundreds of microns.

The optical resolution is therefore not limited the wavelength of light used for observation, but rather by the accuracy an individual fluorescent molecule can be located. This localization accuracy is typically around 20 nm, and depends upon the total number of photons emitted by the molecule prior to photobleaching and the background noise level the molecule is imaged upon. It can be shown that the localization accuracy is strongly dependent upon the background—molecules where only a few photons are detected can still be located to sub-20 nm precision, if done so in a low background environment. Therefore, reducing the background light is important for increasing localization accuracy for a fixed image integration period.

The primary background in these measurements comes from un-activated molecules in the field of view. In particular, an un-activated PA-GFP is not completely dark. As stated hereinabove, the ratio of the fluorescence from an activated PA-GFP to an un-activated PA-GFP is roughly 100:1. The construction of a high-resolution PALM image requires a large density of activatable molecules. For example, assuming that the single molecule stipple points in a final PALM image are ~50 nm apart, then, prior to any activation, a small 0.5 by 0.5 µm field of view contains ~100 photoactivatable fluorophores, which provides a weak fluorescence background. If a single fluorophore in this window is activated on the first PALM cycle, and 250 photons from the activated molecule are measured before it bleaches, the detected photons are measured with a background of approximately an additional 250 photons due to the 100 weakly emitting un-activated molecules also present in the small fitting window. The localization accuracy for this molecule would be quite poor (~320 nm), and the molecule would not be used in the final image reconstruction. Rather, a composite PALM image is formed from "hand-picked" molecules that lie in the tail of two distributions: (a) those that emit a large number of photons prior to bleaching; and (b) the last molecules activated which are imaged in a nearly background-free environment, as all other fluorescent molecules in the field of view have, by this time, photo-bleached. This "cherry-picking" for finding favorable molecules limits the speed of image acquisition: as originally developed, each PALM image required ~1 day to acquire, although use of superior fluorescent proteins has decreased this time to approximately 2 minutes per image.

In "Time-Gated Biological Imaging By Use Of Colloidal Quantum Dots" by M. Dahan et al., Optics Letters 26 (1 Jun. 2001) 825-827, the long fluorescence lifetime of CdSe semiconductor quantum dots was exploited to enhance fluorescence biological imaging contrast and sensitivity by time-gated detection. The inorganic quantum dots emit light slowly enough that most of the autofluorescence background is over by the time emission occurs, but fast enough to maintain a high photon turnover rate.

Advances in this field have extended single-molecule localization methods to three dimensions. In "Tracking of Single Fluorescent Particles In Three Dimensions: Use Of Cylindrical Optics To Encode Particle Position" by H. Pin Kao and A. S. Verkman in Biophysical J. 67 (September 1994) 1291-1300, and in "Three-Dimensional Super-Resolution Imaging By Stochastic Optical Reconstruction Microscopy" by Bo Huang et al. 319 Science (8 Feb. 2008) 810-813, 3D stochastic optical reconstruction microscopy (STORM) has been demonstrated using astigmatism to determine both axial and lateral positions of individual fluorophores with nanometer accuracy using optical astigmatism or ellipticity generated by introducing a cylindrical lens into the imaging path. Bo Huang et al. describe obtaining ~30 nm resolution in 3 spatial dimensions, limited to sparsely labeled cellular structures over a z-depth of less than 1 µm.

SUMMARY OF THE INVENTION

Accordingly, it is an object of the present invention to provide an apparatus and method for imaging materials to better than ~10 nm resolution over hundreds of microns in 3 spatial dimensions.

Another object of the invention is to provide an apparatus and method for imaging materials to better than ~10 nm resolution for densely labeled structures.

Still another object of the invention is to provide an apparatus and method for imaging materials to better than ~10 nm resolution for depths of hundreds of microns.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for 3-dimensional imaging of fluorophore-labeled molecules in a sample, hereof, includes in combination: a pulsed activation laser for generating photons having wavelengths twice the wavelength of a chosen two-photon absorption of the fluorophores, the activation laser having sufficient power to generate two-photon absorption in the fluorophores; a pulsed laser for generating photons effective for producing fluorescence in the fluorophores, when photons from the activation laser are not being directed into the sample; a focusing lens for focusing photons generated by the activation laser and the fluorescence-generating laser onto a chosen area of the sample, and for collecting fluorescence radiation therefrom; means for directing the photons from the activation laser onto the surface of the sample in the x- and y-directions perpendicular to the direction of the photons; means for moving the sample in the z-direction, perpendicular to the plane formed by the x- and y-directions; a camera for measuring the fluorescence from the chosen area of the sample in each z-location; and time-gating means disposed between the focusing lens and the camera for letting fluorescence light reach the camera a chosen time after the pulse of photons from the fluorescence-generating laser impinge on the sample.

In another aspect of the invention, and in accordance with its objects and purposes, the method for 3-dimensional imaging of fluorophore-labeled molecules in a sample, including the steps of: generating pulsed first photons having wavelengths twice the wavelength of a chosen two-photon absorption of the fluorophores, with sufficient power to generate two-photon absorption in the fluorophores; generating pulsed second photons effective for producing fluorescence in the fluorophores, when the first photons are not being directed into the sample; focusing the first photons and the second photons onto a chosen area of the sample, and for collecting fluorescence radiation therefrom; directing the first photons onto the surface of the sample in the x- and y-directions perpendicular to the direction of the first photons; moving said sample in the z-direction, perpendicular to the plane formed by the x- and y-directions; time-gating the fluorescence from the chosen area a selected time after the second photons impinge on the sample and before the step of measuring the fluorescence; and measuring the fluorescence from the chosen area of the sample in each z-location.

Benefits and advantages of the present invention include, but are not limited to providing an apparatus and method for enabling precise, 3-dimension, photoactivation localization microscopy (PALM) using selective, two-photon activation of the fluorophores in a single z-slice of the sample in cooperation with time-gated imaging for reducing the background radiation from other image planes to levels suitable for single-molecule detection and spatial location.

BRIEF DESCRIPTION OF THE DRAWINGS

The accompanying drawing, which is incorporated in and forms a part of the specification, illustrates an embodiment of the present invention and, together with the description, serve to explain the principles of the invention. In the drawing:

The FIGURE is a schematic representation of an embodiment of the two-photon stage-scanning confocal microscope of the present invention.

DETAILED DESCRIPTION OF THE INVENTION

Briefly, the present invention includes an apparatus and method for enabling precise, 3-dimension, photoactivation localization microscopy (PALM) using selective, two-photon activation of the fluorophores in a single z-slice of the sample in cooperation with time-gated imaging for reducing background radiation from other image planes to levels suitable for single-molecule detection and spatial location.

As stated hereinabove, time-gating can essentially eliminate the background (if the background source has a short lifetime) from un-activated molecules enabling precise positional determination for every molecule imaged. In time-gating, a short (typically <100 ps pulse width) pulsed laser is used for fluorescence excitation. Rather than analyzing all photons emitted, only those photons that arrive some fixed time after the laser pulse, are processed. Typically photons arriving at the detector >10 ns after the laser pulse are used in image reconstruction. Time-gating provides a path to 3D reconstruction of samples over depths of hundreds of microns since "un-activated" molecules can become, in essence, totally dark. It should be noted that time-gating is a promising method for reducing background due to Raman scattered excitation laser light, another background interferent, in addition to the background derived from un-activated molecules.

Reference will now be made in detail to the present embodiments of the invention, an example of which are illustrated in the accompanying drawing. In the FIGURE, similar structure will be identified using identical reference characters. Turning now to the FIGURE, a schematic representation of one embodiment of a confocal excitation/detection, stage-scanning confocal microscope, 10, is shown. See, e.g., "Three Dimensional Tracking Of Individual Quantum Dots," by G. Lessard et al. in Appl. Phys. Letts., 91 (2007) 224106-224109, the disclosure of which is hereby incorporated by reference herein. Fluorescence excitation from fluorophores in sample, 12, may be generated from photons, 14, having a wavelength between 720 nm and 920 nm produced by Ti:Saphire activation laser, 16. Pulsewidths generally lie within the range of 100-120 fs full-width at half-maximum. Read-out photons, 18, may be provided from the pulse train of mode-locked Argon ion laser, 20, having a wavelength of 488 nm and pulse width of ~100 ps, and are used to read an entire image plane of sample 12 with blue light. Shutter, 21, blocks photons 18 when sample 12 is being activated by photons 14.

It should be mentioned that other light sources, such as light emitting diodes (LEDs), may be employed for sources of read-out photons. For pulsed light sources, shutter 21 would not be needed. First Galvanic mirror, 22, and second Galvanic mirror, 24, sweep photons 14 in the x- and y-directions, respectively, thereby activating a single location on sample 12 which location is rastered over an entire z-slice for each value of z, while reflecting dichroic mirror, 26, reflects photons 14 and 18 through confocal objective lens, 28, onto sample 12. Sample 12 may be located on stage, 30, which is driven in the z-direction, 32, by stepping motor or piezoelectric translator, 34. Fiducial marks (for example an immobilized quantum dot or piece of colloidal gold) can be used to compensate for instrument drift during these high-resolution imaging methods. In addition to this method, active real-time feed back of a 3-D piezoelectric stage can be used to compensate for sample drift, which has the potential for sub-nm correction accuracy in three spatial dimensions.

Fluorescence photons, 36, are collected and collimated using objective 26, pass through dichroic mirror 26, and may be collected by cylindrical lens, 38, which encodes the z-position by astigmatic collection. The collected fluorescence may be directed into camera 40. Signal processor, 42, receives the signal from camera 40, and processes this signal, as will be described hereinbelow. The functions of computer controller, 44, include control of the location of sample 12, the operation of lasers 16 and 20, the angles of mirrors 22 and 24, for rastering excitation photons 14 over the surface of a z-slice of sample 12, and the gating of camera 40.

Stage-scanning of a sample is generally a slow process (~1 ms per pixel). However, time-gating in a wide-field (CCD readout) platform will be performed such that rapid image acquisition (a 100 μm by 100 μm field of view in approximately 100 ms) may be enabled. To achieve wide-field, time-gated imaging, fast image intensifier, 46, acting as a high-speed, high repetition rate shutter (~100 ps timing resolution, turning with an 80 MHz switching rate, and with an extinction ratio of ~100) may be utilized as part of camera 40, and may be interfaced to an electron-multiplying CCD camera. Dark counts for a CCD camera are ~0.05 photoelectrons/s/pixel and the read noise is effectively less than 1 photoelectron per pixel when using on-chip gain. It is therefore unlikely that noise from the camera will become the dominant background contributor.

In order to form 3-dimensional images, a single slice (in z) of the photo-activatable fluorophores is selectively activated, which can then by imaged in a wide-field (x,y) mode. Two-photon activation of the fluorophores will preferentially activate a single thin layer in the sample, since the simultaneous absorption of two photons of near infra-red light from a mode-locked excitation laser occurs only near the waist of a tightly focused excitation laser beam, due to the nonlinear nature of the excitation process, in contrast to the use of a single UV photon. It has been demonstrated by M. Schneider et al., supra, that molecules within a z-slice of approximately ~3 μm in depth can be selectively activated. Different sequential slices in the sample (for example, 2 μm steps in z between 0 and 100 μm) can be selectively activated for 3-D image reconstruction.

Resolution in the z-dimension is not limited by the height of the activated layer; a more precise determination of the "z" depth of the activated molecules may be achieved by analyzing the image shape on the CCD. For example, a weak cylindrical lens may be placed in the optical detection path, such that molecules lying precisely in the image plane of the sample appear to be "round," whereas molecules above and below the image plane will appear to be oval shaped. See, for example, H. Pin Kao et al., supra. Molecules above and below the image plane have the primary axis of their ellipsoidal images rotated 90° with respect to each other. Using this method, H. Pin Kao et al. have determined the z-location of polystyrene beads with ~13 nm accuracy. More recently, this method has been expanded to single molecule localization, with ~40 nm accuracy in z, obtainable in fixed cells. With background suppression enabled by time-gating, resolutions of ~20 nm in z and better than 10 nm in x and y should be attainable. As is the case for 2-D localization, 3-D localization accuracy in accordance with the present invention is dependent upon the number of photons which can be recorded prior to photo-bleaching the fluorophore, as well as the background from the sample.

Two-photon activation may slow the single-molecule localization process since two-photon activation requires scanning a tightly focused excitation laser beam for activation, rather than activating all of the molecules at once in a wide-field fashion as is done in conventional single-molecule localization. It is expected that a few molecules in a 100 μm by 100 μm, x,y raster scan at an appropriate z-depth should be activated in a few seconds; fast enough to acquire the multiple z-slices/day needed for routine 3-dimensional rendering. If photo-activation speed becomes a bottleneck to image acquisition, a multi-focus approach to multi-photon activation may be pursued. This approach for rapid (video-frame rate) multi-photon imaging, uses a rotating multi-lens disk to create an array of excitation foci within the sample.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for 3-dimensional imaging of fluorophore-labeled molecules in a sample, comprising in combination:
    a pulsed activation laser for generating photons having wavelengths twice the wavelength of a chosen two-photon absorption of the fluorophores, said activation laser having sufficient power to generate two-photon absorption in the fluorophores;
    a pulsed light source for generating photons effective for producing fluorescence in the fluorophores, when photons from said activation laser are not being directed into said sample;
    a focusing lens for focusing photons generated by said activation laser and said fluorescence-generating laser onto a chosen area of said sample, and for collecting fluorescence radiation therefrom;
    means for directing the photons from said activation laser onto the surface of said sample in the x- and y-directions perpendicular to the direction of the photons;
    means for moving said sample in the z-direction, perpendicular to the plane formed by the x- and y-directions;
    a camera for measuring the fluorescence from the chosen area of said sample in each z-location; and
    time-gating means disposed between said focusing lens and said camera for letting fluorescence light reach said camera a chosen time after the pulse of photons from said fluorescence-generating laser impinges on said sample.

2. The apparatus of claim 1, further comprising a cylindrical lens between said time-gating means and said focusing lens.

3. The apparatus of claim 1, wherein said time-gating means comprises an image intensifier.

4. The apparatus of claim 1, wherein said camera comprises a charge-coupled camera.

5. The apparatus of claim 1, wherein said fluorophores are selected from the group consisting of photoactivatible green fluorescent protein and fluorescein.

6. A method for 3-dimensional imaging of fluorophore-labeled molecules in a sample, comprising the steps of:
    generating pulsed first photons having wavelengths twice the wavelength of a chosen two-photon absorption of the fluorophores, with sufficient power to generate two-photon absorption in the fluorophores;
    generating pulsed second photons effective for producing fluorescence in the fluorophores, when the first photons are not being directed into the sample;
    focusing the first photons and the second photons onto a chosen area of the sample, and for collecting fluorescence radiation therefrom;
    directing the first photons onto the surface of the sample in the x- and y-directions perpendicular to the direction of the first photons;
    moving said sample in the z-direction, perpendicular to the plane formed by the x- and y-directions;
    time-gating the fluorescence from the chosen area a selected time after the second photons impinge on the sample; and
    measuring the time-gated fluorescence from the chosen area of the sample in each z-location.

7. The method of claim 6, further comprising the step of directing the fluorescence from the chosen area through a cylindrical lens before said step of measuring the time-gated fluorescence.

8. The method of claim 6, wherein said step of time-gating the fluorescence is performed using an image intensifier.

9. The method of claim 6, wherein said step of measuring the time-gated fluorescence is performed using a charge-coupled camera.

10. The method of claim 6, wherein the fluorophores are selected from the group consisting of photoactivatible green fluorescent protein and caged fluorescein.

* * * * *